(12) United States Patent
Caron et al.

(10) Patent No.: US 8,978,447 B2
(45) Date of Patent: Mar. 17, 2015

(54) POROUS MEDIUM SENSOR

(75) Inventors: Jean Caron, Saint-Romuald (CA); Daniel Belleau, Sainte-Hélène de Breakeyville (CA); Jocelyn Boudreau, St-Lambert-de-Lauzon (CA); Sébastien Rochette, Québec (CA)

(73) Assignee: Hortau, Inc., Saint-Romuald, Quebec (CA)

( * ) Notice: Subject to any disclaimer, the term of this patent is extended or adjusted under 35 U.S.C. 154(b) by 308 days.

(21) Appl. No.: 13/591,932

(22) Filed: Aug. 22, 2012

(65) Prior Publication Data

US 2014/0053633 A1 Feb. 27, 2014

(51) Int. Cl.
| G01N 15/08 | (2006.01) |
| G01N 33/24 | (2006.01) |
| G01N 13/02 | (2006.01) |
| G01N 33/26 | (2006.01) |

(52) U.S. Cl.
CPC ............... *G01N 13/02* (2013.01); *G01N 33/26* (2013.01)
USPC .................................................. 73/38; 73/73

(58) Field of Classification Search
CPC ....... A01G 25/167; G01N 7/10; G01N 15/08; G01N 33/24; G01N 33/246
USPC ........................................................ 73/38, 73
See application file for complete search history.

(56) References Cited

U.S. PATENT DOCUMENTS

| 4,845,978 A * | 7/1989 | Whitford ........................... 73/73 |
| 4,874,426 A | 10/1989 | Honda |
| 4,909,070 A | 3/1990 | Smith |
| 5,046,282 A | 9/1991 | Whitaker |
| 5,179,347 A | 1/1993 | Hawkins |
| 5,219,388 A * | 6/1993 | Meletiou et al. ........... 73/152.31 |
| 5,520,248 A | 5/1996 | Sisson et al. |
| 5,546,217 A | 8/1996 | Greenway |

(Continued)

FOREIGN PATENT DOCUMENTS

| DE | 10047937 | 4/2002 |
| DE | 10121326 | 2/2003 |

(Continued)

OTHER PUBLICATIONS

Keller, Thomas; et al., T5/T5xx—Pressure Transducer Tensiometer, UMS measure to know, 2009, 48 pages, Art.Nr. T5, Version Dec. 2009, and UMS GmbH München.

*Primary Examiner* — Daniel S Larkin
(74) *Attorney, Agent, or Firm* — Price Heneveld LLP (57) ABSTRACT

A porous medium sensor comprises: a sensing portion, a gas exchange tubing, a gas permeable protection sleeve, and a water impermeable distal end collar. The sensing portion is at least partially insertable in a porous medium and has a housing with a gas exchange aperture defined therein and a parameter sensor mounted in the housing for measuring a parameter of the porous medium in which the sensing portion is insertable. The gas exchange tubing is in gas communication with the gas exchange aperture of the sensor portion and has a water-repellent membrane inserted therein. The water-repellent membrane prevents water infiltration in the housing through the gas exchange aperture. The gas permeable protection sleeve covers at least a section of the gas exchange tubing. The water impermeable distal end collar covers a distal end of the gas permeable protective sleeve and the water-repellent membrane.

20 Claims, 5 Drawing Sheets

(56) References Cited

U.S. PATENT DOCUMENTS

| | | | |
|---|---|---|---|
| 5,644,947 A * | 7/1997 | Hubbell et al. | 73/73 |
| 5,677,949 A | 10/1997 | Macor | |
| 5,758,538 A | 6/1998 | Hubbell et al. | |
| 5,816,704 A | 10/1998 | Campbell et al. | |
| 5,915,476 A | 6/1999 | Hubbell et al. | |
| 5,969,242 A | 10/1999 | Hubbell et al. | |
| 6,289,725 B1 | 9/2001 | Hubbell et al. | |
| 6,308,563 B1 | 10/2001 | Hubbell et al. | |
| 6,405,588 B1 | 6/2002 | Hubbell et al. | |
| 6,539,780 B2 | 4/2003 | Hubbell et al. | |
| 6,609,434 B2 | 8/2003 | Hubbell et al. | |
| 6,752,007 B1 | 6/2004 | Hubbell et al. | |
| 6,772,621 B2 | 8/2004 | Grover et al. | |
| 6,826,972 B2 | 12/2004 | Clark et al. | |
| 6,904,789 B2 | 6/2005 | Campbell et al. | |
| 6,920,780 B2 | 7/2005 | Hubbell et al. | |
| 6,938,461 B1 | 9/2005 | Johnson | |
| 6,986,281 B1 | 1/2006 | Hubbell et al. | |
| 7,005,662 B2 | 2/2006 | Caron et al. | |
| 7,178,391 B2 | 2/2007 | Casper et al. | |
| 7,311,011 B2 | 12/2007 | Clark et al. | |
| 7,437,957 B2 | 10/2008 | Jobin et al. | |
| 7,617,742 B2 | 11/2009 | Radtke et al. | |
| 7,806,585 B2 | 10/2010 | Fontana, Jr. et al. | |
| 8,058,885 B2 | 11/2011 | Caron | |
| 2003/0121336 A1 * | 7/2003 | Hubbell et al. | 73/863.23 |
| 2004/0083835 A1 | 5/2004 | Casper et al. | |
| 2006/0043300 A1 | 3/2006 | Campbell et al. | |
| 2010/0263436 A1 | 10/2010 | Caron et al. | |

FOREIGN PATENT DOCUMENTS

| | | |
|---|---|---|
| DE | 102004056178 | 6/2006 |
| DE | 202009000639 | 4/2009 |
| DE | 202009000641 | 4/2009 |
| EP | 1396722 | 3/2004 |

\* cited by examiner

POROUS MEDIUM SENSOR

BACKGROUND OF THE INVENTION

1. Field of the Invention

The invention relates to porous medium sensors for measuring parameters or properties in porous media and, more particularly, it relates to a porous medium sensor having a sensing portion insertable in the porous medium with a reference port in gas communication with ambient air.

2. Description of the Prior Art

Porous medium sensors for monitoring parameters in soil are known. For example, tensiometers monitor matrix water potential $\psi_m$ (or soil moisture tension), which is an indirect measure of soil water content. Tensiometers are used in irrigation scheduling to help farmers and other irrigation managers to determine when to water. Tensiometers can also be used in the scientific study of soil and plant behaviors.

Typically the porous medium sensors are partially inserted in growing media, such as soil, for monitoring purposes. They include a sensing portion which is insertable in the growing medium and a head which extends outwardly. A section of the housing can also extend outwardly of the growing medium.

Several porous medium sensors, such as tensiometers, have a reference port in gas communication with ambient air. The reference port can be either immersed in the growing medium or located outwardly of the growing medium when a sensing portion of the porous medium sensor is inserted therein. Water and porous medium infiltration into the reference port, can bias measurements taken in the growing medium, even if the latter is located above the growing medium. To prevent this problem, it is known to cover the reference port with a water-repellent membrane [See for instance U.S. patent application no. 2010/0263436 filed on Apr. 30, 2010].

However, the water-repellent membrane can seal in heavy growing media, for instance the ones having high clay content. Furthermore, if the water-repellent membrane is inserted in a fine growing media, a trapped volume of air can surround the water-repellent membrane and also bias the soil property measurements. Furthermore, water-repellent membranes do not perfectly repel water in all conditions, particularly if the soil becomes hydrophobic. In particular conditions, water and/or small particles can thus infiltrate the sensor through the reference port.

BRIEF SUMMARY OF THE INVENTION

It is therefore an aim of the present invention to address the above mentioned issues.

According to an aspect, there is provided a porous medium sensor comprising: a sensing portion at least partially insertable in a porous medium and having a housing with a gas exchange aperture defined therein and a parameter sensor mounted in the housing for measuring a parameter of the porous medium in which the sensing portion is insertable; a gas exchange tubing in gas communication with the gas exchange aperture of the sensor portion and having a water-repellent membrane inserted therein, the water-repellent membrane preventing water infiltration in the housing through the gas exchange aperture; a gas permeable protection sleeve covering at least a section of the gas exchange tubing; and a water impermeable distal end collar covering a distal end of the gas permeable protective sleeve and the water-repellent membrane.

According to another aspect, there is provided a porous medium sensor comprising: a sensing portion at least partially insertable in a porous medium and having a housing with a gas exchange aperture defined therein and a parameter sensor mounted in the housing for measuring a parameter of the porous medium in which the sensing portion is insertable; a gas exchange tubing having a gas and water impermeable wall defining a gas exchange channel in gas communication with the gas exchange aperture of the sensing portion and a water-repellent membrane inserted in the gas exchange channel, the water-repellent membrane preventing water infiltration in the gas exchange channel through a distal open end of the gas exchange tubing; a gas permeable sleeve covering at least partially the gas exchange tubing and allowing gas communication with the water-repellent membrane; and a water impermeable distal end collar covering at least a section of the gas permeable sleeve and a section of the gas exchange tubing including the water-repellent membrane to prevent water infiltration therein.

In this specification, the term "porous medium" is intended to mean the soil of a field in agriculture, or the soil of pots for growing plants in a greenhouse or in a nursery, and any porous medium which fills with liquid. It can also be called a substrate, a mixture, a medium, or a soilless medium.

In this specification, the term "water-repellent" is defined as having a degree of resistance to permeability by and to damage caused by water in liquid form and therefore encompasses the common terms of "waterproof" and "hydrophobic".

The present document refers to a number of documents, the contents of which are hereby incorporated by reference in their entirety.

BRIEF DESCRIPTION OF THE DRAWINGS

It will be noted that throughout the appended drawings, like features are identified by like reference numerals.

DETAILED DESCRIPTION

Figure 1:
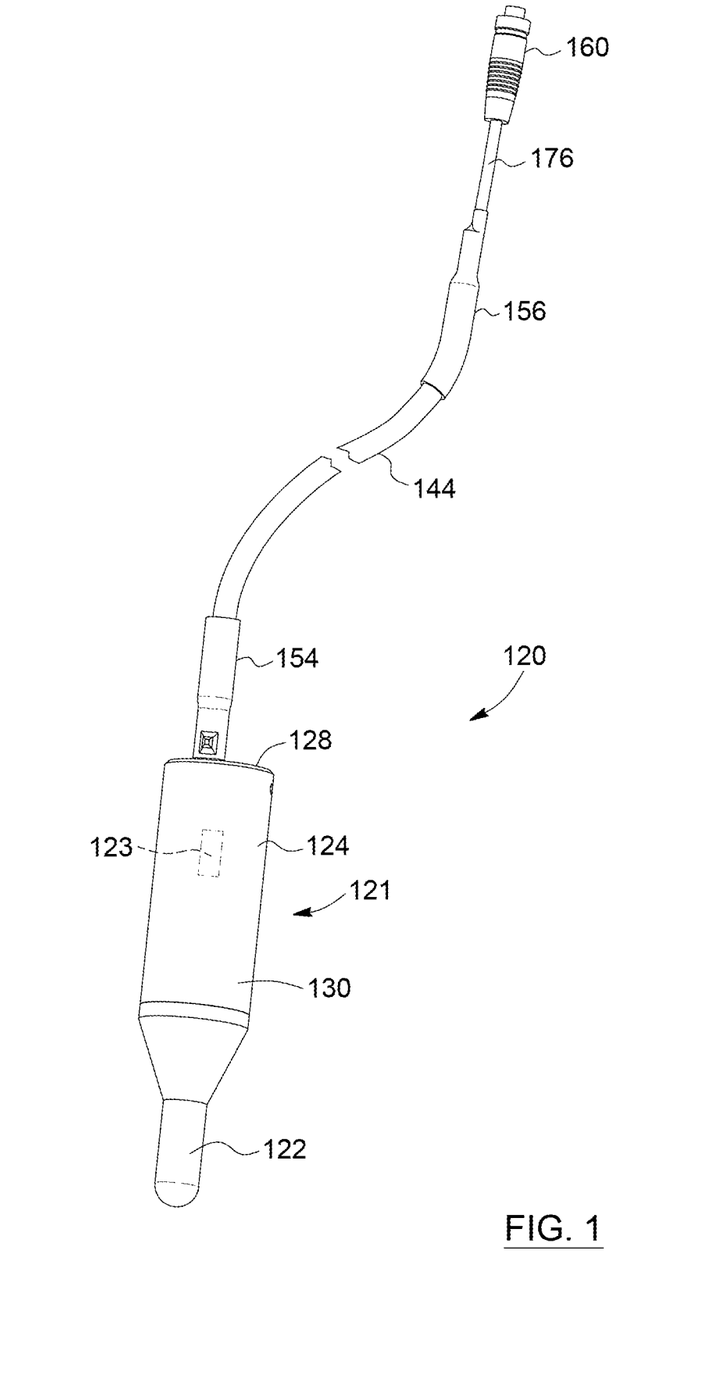
FIG. 1 is a perspective view of the porous medium sensor in accordance with an implementation.

Referring to the drawings and, more particularly, to FIG. 1, there is shown a porous medium sensor 120 and, more particularly, a tensiometer apparatus (or water potential sensor) in accordance with an embodiment. The tensiometer is designed to monitor matrix water potential in a porous medium such as, for instance, earthen soil or greenhouse soil.

The porous medium sensor 120 has a sensing portion 121 with a housing 124 and a porous material tip 122. The porous material tip 122 extends outwardly from the housing 124 and is in direct contact with the porous medium when inserted therein. The housing 124 encloses a parameter sensor 123 (schematically represented in FIG. 1) for measuring a parameter of the porous medium in which the sensing portion 121 is inserted. The sensing portion 121 is designed to be at least partially inserted in the porous medium. In some implementations, the sensing portion 121, such as the one shown in FIG. 1, is designed to be wholly inserted in the porous medium.

The design, the shape, and the components of the porous medium sensor 120 can vary from the above-described and illustrated embodiment.

The housing 124 has a gas exchange aperture 125 (FIG. 4) extending throughout an upper wall 128 thereof. In some implementations, the gas exchange aperture can extend throughout any wall of the housing 124, such as and without being limitative, the lateral wall 130 of the housing 124. When the sensing portion 121 is partially or totally inserted in the porous medium, the gas exchange aperture can also be located in the porous medium. In the implementation shown in FIG. 1, the sensing portion 121 is totally insertable in the porous medium with the gas exchange aperture located in the porous medium.

The gas exchange aperture is a reference port of the porous medium sensor 120. The gas exchange aperture is conceived to allow gas exchange between air located outside the housing, i.e. ambient air, and an internal component (not shown) of the housing 124. For the tensiometer shown in FIGS. 1 to 5, the gas exchange aperture is in gas communication with a pressure sensor (not shown) mounted in the housing 124. The pressure sensor compares the liquid pressure in a fluid chamber to the atmospheric pressure, which is provided through the gas exchange aperture, which is in gas communication with atmospheric gas.

Figure 3:
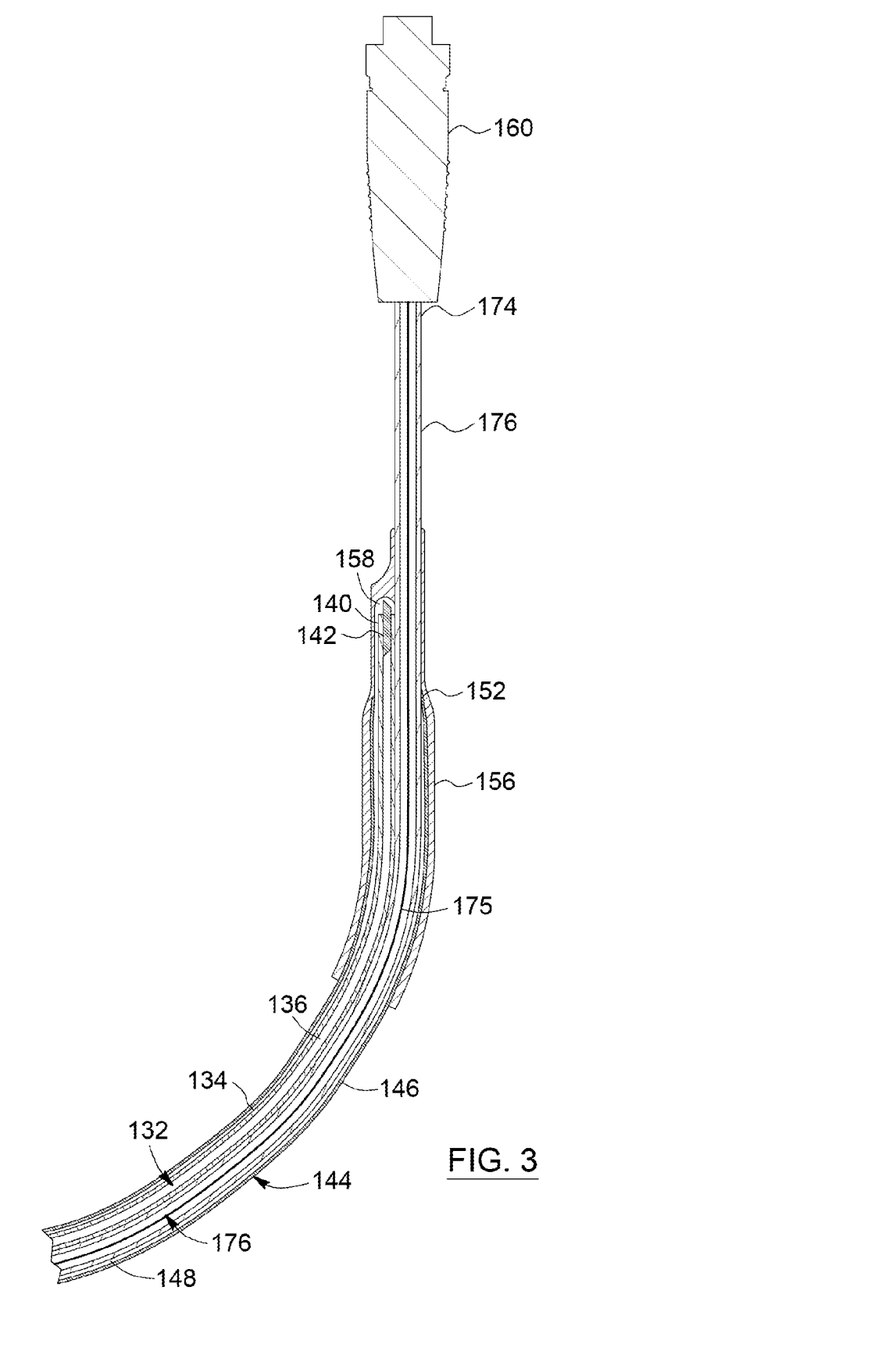
FIG. 3 is a cross-section view of the distal section of the porous medium sensor shown in FIG. 2.
Figure 5:
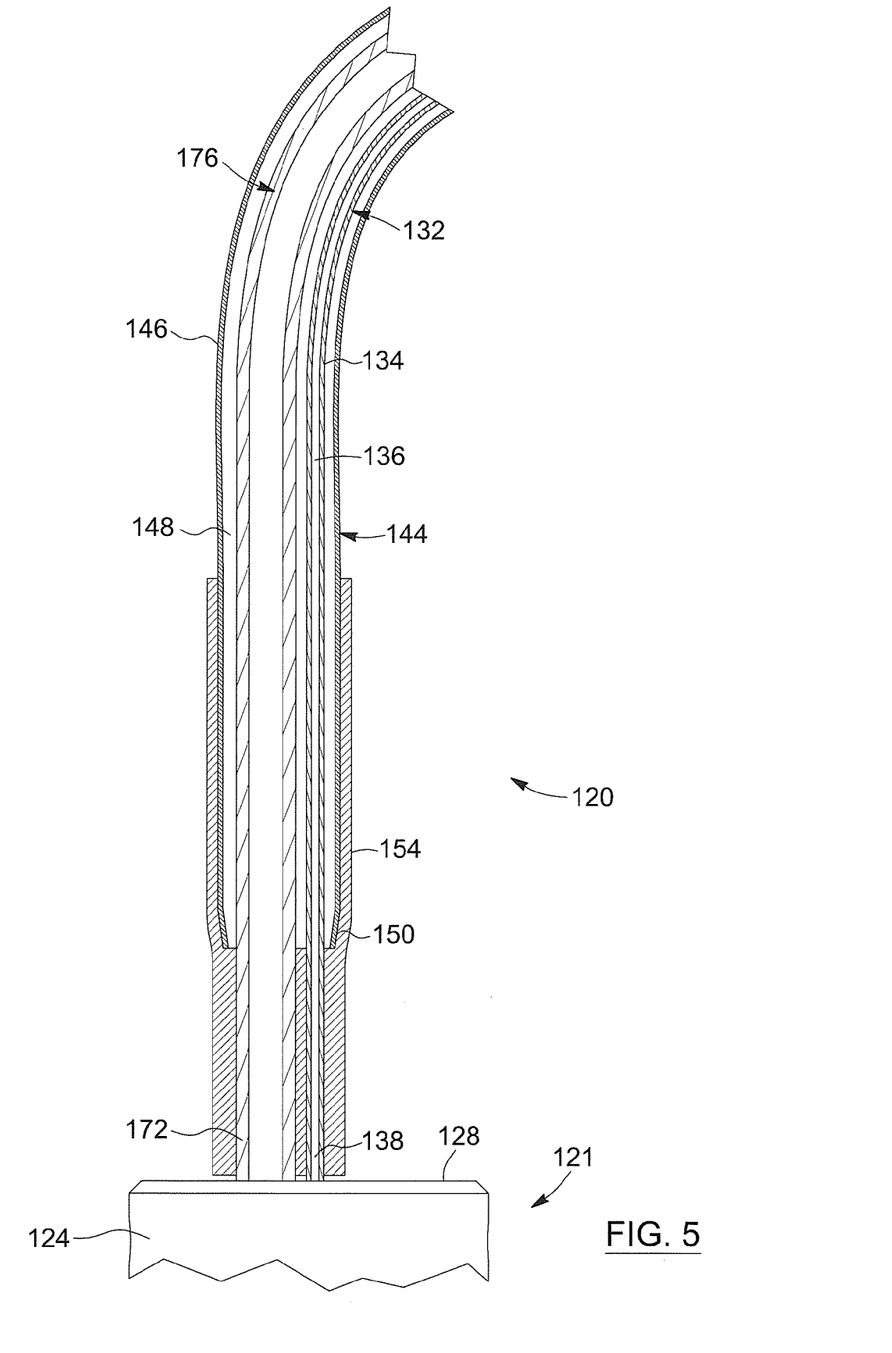
FIG. 5 is a cross-section view of the distal section of the porous medium sensor shown in FIG. 4.

Referring now to FIGS. 3 and 5, there is shown that, to prevent liquid such as water and porous medium infiltration in the gas inlet aperture and pressure variation due to porous medium surrounding the gas exchange aperture, the gas exchange aperture is connected to a gas exchange tubing 132. The gas exchange tubing 132 is a tubular member with a peripheral wall 134 that defines a gas exchange channel 136. A proximal end 138 of the gas exchange tubing 132 is sealed to the housing 124 with the gas exchange channel 136 being aligned with the gas exchange aperture and in gas communication therewith. The gas exchange tubing 132 is a flexible and elongated tubing made of a gas and liquid (water) impermeable material. Therefore, gas exchange with the gas exchange aperture occurs through the internal gas exchange channel 136. In some implementations (without limitation), the gas exchange tubing 132 is made of nylon, Tygon®, water impermeable plastics, rubber or any other water impermeable tubing.

Figure 2:
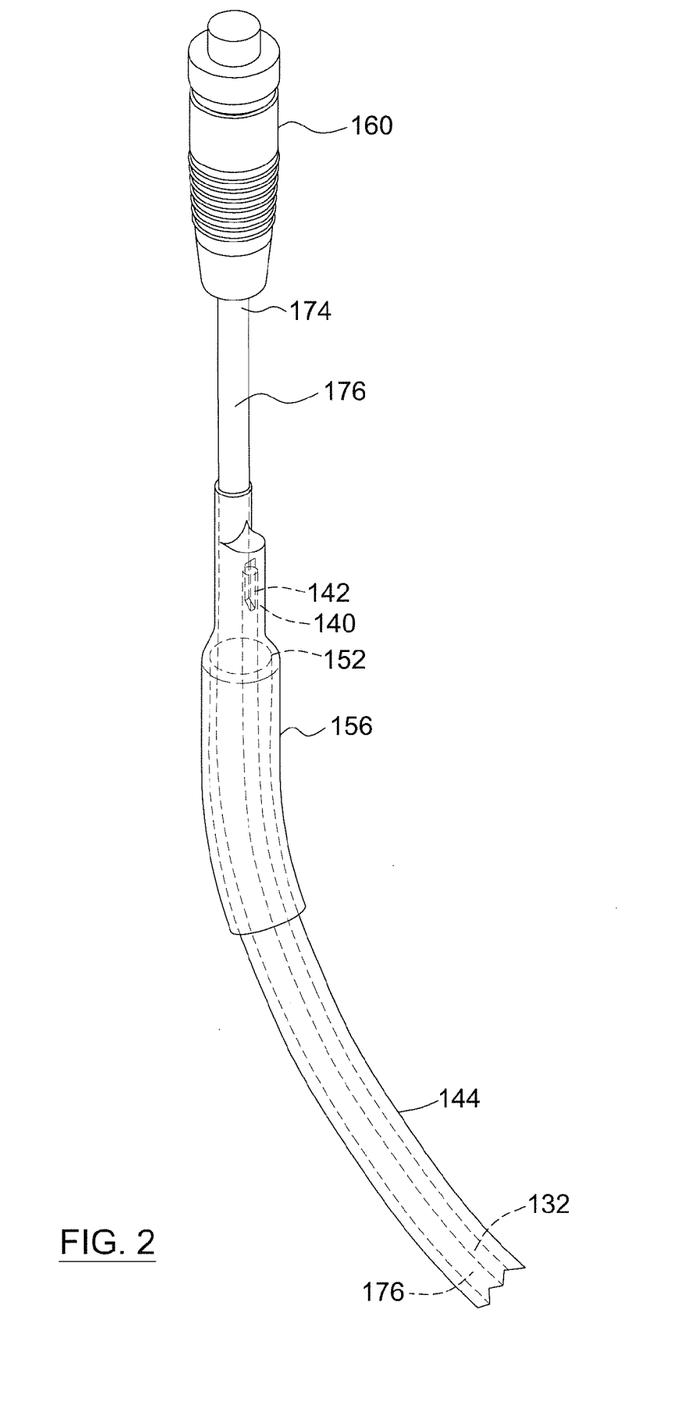
FIG. 2 is a perspective view, enlarged and fragmented, of a distal section of the porous medium sensor shown in FIG. 1.
Figure 4:
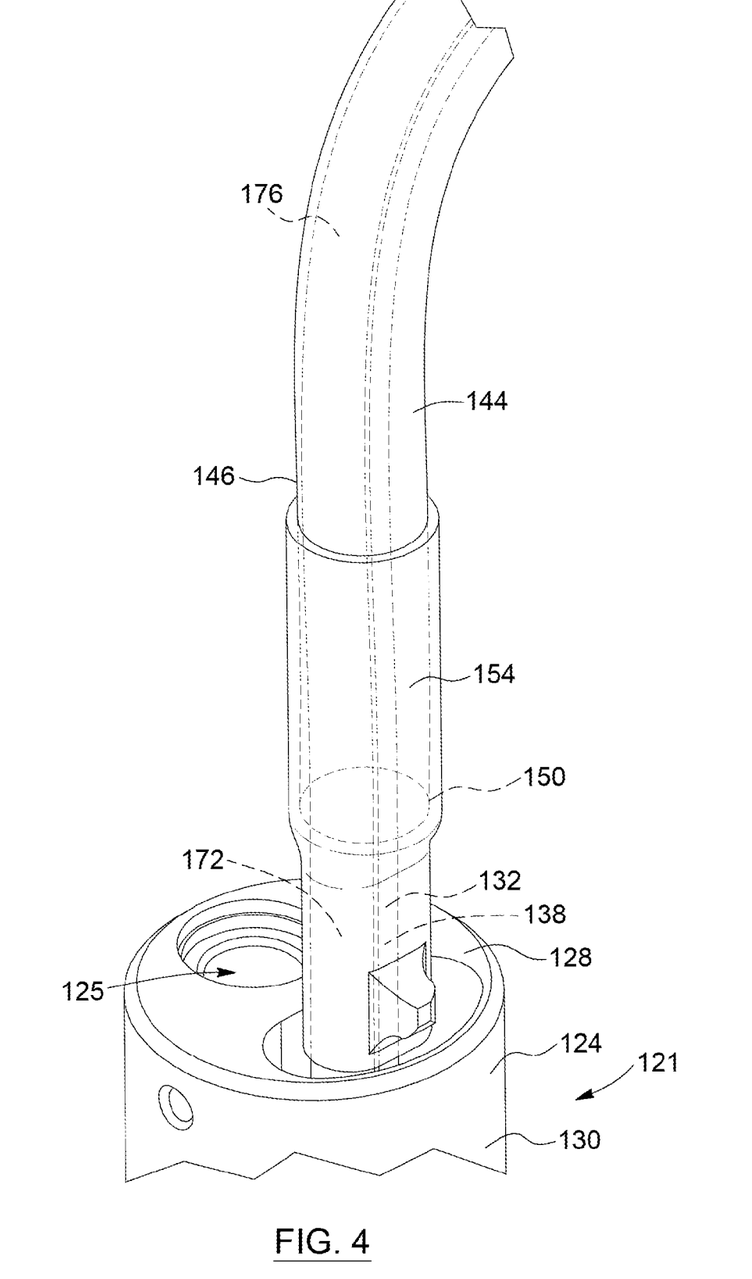
FIG. 4 is a perspective view, enlarged and fragmented, of a proximal section of the porous medium sensor shown in FIG. 1.

Referring now to FIGS. 2 and 3, there is shown that the gas exchange tubing 132 has a distal end 140, opposed to the proximal end 138 shown in FIGS. 4 and 5. To prevent water, growing medium particle or insect infiltration in the gas exchange channel 136, which could flow in the housing 124 through the gas exchange aperture, a water-repellent membrane 142 is inserted in the gas exchange channel 136, close to the distal end 140. In an embodiment, the water-repellent membrane 142 is inserted in the gas exchange channel 136 in less than about 1 inch from the distal end 140 of the gas exchange tubing 132. Gas exchange between atmosphere and the housing 124 occurs through the water-repellent membrane 142, the gas exchange channel 136, and the gas exchange aperture.

The water-repellent membrane 142 is porous and gas permeable, i.e. it allows gas communication between atmosphere and the housing 124. The pressure on both sides of the water-repellent membrane 142 is substantially equal. The response time of the water-repellent membrane 142 to reach equilibrium is substantially fast. In an embodiment, the water-repellent membrane 142 can substantially resist microbiologic and chemical degradation. The membrane shape, thickness, and size can vary in accordance with the porous medium sensor design.

The water-repellent membrane 142 is shaped to fill the gas exchange channel 136 defined in the gas exchange tubing 132 and is tightly inserted therein. If an adhesive is used to secure the water-repellent membrane 142 to the gas exchange tubing 132, care should be taken to prevent or minimize membrane pore obstruction with the adhesive.

For instance, without being limitative, Teflon®, hydrophobic polypropylene and polyethylene porous sheets, manufactured with free-sintered materials, such as resins, glass, or metal beads can be used. These porous sheets provide filter media for ultrafine particles and flowability of gases. The filtration obtained varies depending on the micron size material selected.

The porous medium sensor 120 further includes one or a plurality of electric wires 175 (FIG. 3) having a proximal end operatively connected to internal component(s) of the housing 124 and extending outwardly therefrom. The electric wire(s) have an opposed distal end which can be connected to a head (not shown) of the porous medium sensor 120 through an electric connector 160 operatively connected to the electric wire distal end. The head can include an electric circuit board (not shown) of the porous medium sensor 120. The electric wire(s) transfers data acquired or monitored by the sensor 120 to the electronic circuit board for further processing. The electric wire(s) can also provide a power supply to the sensor 120 and an electric/electronic circuit operatively connected to the sensor 120. The head can extend above the porous medium when the sensing portion 120 is at least partially inserted therein.

In the embodiment shown, the electric wire(s) are surrounded by a common sleeve 176 which extends between the housing 124 and the porous medium head. The electric wire sleeve 176 has a proximal end 172 close to the housing 124 and a distal end 174 with the electric connector 160 mounted thereto for connection to the head (not shown). The electric wires and the electric wire sleeve 176, if any, can extend along the gas exchange tubing 132.

In the embodiment shown, the electric wire sleeve 176 and the gas exchange tubing 132 are flexible components. In some implementations, the electric wire sleeve 176 and/or the gas exchange tubing 132 can be rigid components.

The porous medium sensor 120 further includes a protection sleeve 144 surrounding at least a section of the gas exchange tubing 132. In the embodiment shown, the protection sleeve 144 also surrounds the electric wire sleeve 176 surrounding the electric wire(s). The protection sleeve 144 is a tubular member with a peripheral wall 146 that defines an internal gas channel 148. At least a section of the gas exchange tubing 132 extends in the internal gas channel 148. The protection sleeve 144 has a proximal end 150, close to the housing 124 (shown in FIGS. 4 and 5), and an opposed distal end, close to the distal end 140 of the gas exchange tubing 132 (shown in FIGS. 2 and 3).

The protection sleeve 144 is a flexible and elongated tubing made of gas permeable material. Furthermore, in some implementations, the protection sleeve 144 is rodent resistant (or anti-rodent). In an embodiment, the protection sleeve 144 includes a metal wire mesh component such as a woven metallic component to offer a protection against rodent damage.

In some implementations, the protection sleeve 144 covers the section of the gas exchange tubing 132 including the water-repellent membrane 142. In other implementations, the protection sleeve 144 does not cover the section of the gas exchange tubing 132 including the water-repellent membrane 142, the latter being covered solely by an end collar, as described in more details below.

In some implementations, the protection sleeve 144 is made of woven material like fiberglass, metals, plastics or natural fiber clothing or non woven geotextile, fiberglass or metals.

Referring back to FIG. 1, there is shown that the porous medium sensor 120 further includes a proximal end collar 154 and a distal end collar 156. Referring now to FIGS. 4 and 5, there is shown that the proximal end collar 154 has a first end sealed to the gas exchange tubing 132 and the electric wire sleeve 176, and a second end sealed to the protection sleeve 144. In some implementations, the first end of the proximal end collar 154 can be sealed to the housing 124.

If the protection sleeve 144 directly surrounds the electric wire(s), the first end of the proximal end collar 154 can be sealed to the electric wire(s) and the gas exchange tubing 132.

Referring now to FIGS. 2 and 3, there is shown that the distal end collar 156 has a first end sealed to the protection sleeve 144 and a second end. The second end can be a closed end, if the protection sleeve 144 does not surround the electric wire(s) or the electric wire sleeve 176. In an alternative embodiment, the second end can be sealed to the electric wire(s) or the electric wire sleeve 176, if any. In the embodiment shown, the second end of the distal end collar 156 is sealed to the electric wire sleeve 176, which extends past the distal end collar 156.

In the embodiment shown in the figures, the electric wires are assembled together and surrounded by the electric wire sleeve 176. The protection sleeve 144 surrounds the gas exchange tubing 132 and the electric wire sleeve 176. The proximal end collar 154 surrounds the assembly including the gas exchange tubing 132, the electric wire sleeve 176, and the protection sleeve 144. The first end of the proximal end collar 154 is sealed to the gas exchange tubing 132 and the electric wire sleeve 176 as there is a spacing between the protection sleeve 144 and the housing 124. The second end of the proximal end collar 154 is sealed to the protection sleeve 144. The distal end collar 156 surrounds the assembly including the gas exchange tubing 132, the electric wire sleeve 176, and the protection sleeve 144 with its first end sealed to the protection sleeve 144. The second end is sealed to the electric wire sleeve 176, which extends outwardly past the distal end collar 156. The gas exchange tubing 132 and the protection sleeve 144 have their distal ends 140, 152 located inside the distal end collar 156. The water-repellent membrane 142 is also covered by the distal end collar 156.

The distal end collar 156 covers a free end of the protective sleeve 144, a free end of the gas exchange tubing 132, and the water-repellent membrane 142.

The proximal end collar 154 and the distal end collar 156 are made of a water impermeable material and, in an embodiment, a gas barrier material. For instance, the collars 154, 156 can be made of a thermo shrinkable polymer such as and without being limitative any rigid or flexible water impermeable material like rubber, water impermeable plastics, nylon or metals.

Referring to FIG. 3, there is shown that the internal channel 148 of the protection sleeve 144 has a diameter larger than the combined outer diameter of the electric wire sleeve 176 and the gas exchange tubing 132. Thereby, a gas channel extends longitudinally therein through which air and other gases can circulate. The gas channel allows air to reach the water-repellent membrane 142 housed in the gas exchange tubing 132. In an alternative implementation (not shown), the apparatus can be free of gas channel since the protection sleeve 144 is air permeable.

The distal end of the apparatus further includes a gas chamber 158 defined above the water-repellent membrane 142.

The gas chamber 158 allows gas exchange between atmosphere and the gas exchange channel 136 through the protection sleeve 144 and the water-repellent membrane 142. The gas chamber 158 is defined inside the distal end collar 156, i.e. the distal end collar 156 is not sealed to the water-repellent membrane 142. Thus, gas exchange between atmosphere and the gas exchange channel 136 occurs through the protection sleeve 144, the gas channel, if any, the gas chamber 158, and the water-repellent membrane 142.

In an embodiment (not shown), the protection sleeve 144 can extend past the water-repellent membrane 142 and define the gas chamber 158 in the section of the internal gas channel 148 extending past the water-repellent membrane 142. In other words, the section of the protection sleeve 144 which extends past the water-repellent membrane prevents the distal end collar 156 from abutting the water-repellent membrane 142 and thereby prevents gas exchange.

When the sensing portion 121 of the porous medium sensor 120 is at least partially inserted in the porous medium, a section of the assembly including the gas exchange tubing 132, the electric wire sleeve 176, and the protection sleeve 144 is located outwardly of the porous medium. This section further includes the distal end collar 156. Gas exchange between the housing 124 and atmosphere occurs through the protection sleeve 144, which is gas permeable, the internal gas channel 148 extending in the protection sleeve 144, the gas exchange channel 136 including the water-repellent membrane 142, and the gas exchange aperture of the housing 124.

Liquid infiltration in the gas exchange aperture of the housing 124 is prevented through both the distal end collar 156 and the water-repellent membrane 142. The distal end collar 156 prevents important water quantity and particles to reach the water-repellent membrane 142.

In the embodiment shown, the protection sleeve 144 extends along substantially the length of the gas exchange tubing 132. However, in some implementations, the protection sleeve 144 can extend along a shorter section thereof. In the embodiment shown, the distal end of the assembly, including the distal end collar 156 covering the water-repellent membrane 142, prevents partial or complete obstruction of the gas exchange aperture or a portion of the housing 124 which could bias the pressure or other porous medium property measurements.

To measure a porous medium property, such as matrix water potential, in a porous medium, the sensing portion 121 is first inserted in the porous medium. The assembly including the gas exchange tubing 132, the electric wire sleeve 176, the protection sleeve 144, and the distal end collar 156 extends upwardly with their distal ends extending outwardly of the porous medium.

Once the sensing portion 121 is connected to a power supply (not shown), if needed, the porous medium sensor 120 monitors the porous medium property in the porous medium where the sensing portion 121 is inserted. Gas exchange with the housing 124 inserted in the porous medium and atmospheric pressure therein is ensured through the gas permeable protection sleeve 144, the gas exchange channel 136 having the water-repellent membrane 142 inserted therein, and the gas exchange aperture. Therefore, for pressure measurement purposes, it is assumed that gas pressure within the porous medium, at the sensing portion insertion depth, is substantially similar to atmospheric pressure. The monitored data are transferred to an electronic circuit board which can display, transmit and/or record the data.

Liquid and porous material infiltration is prevented by the combination of the water-repellent membrane 142 and the distal end collar 156, even if the gas exchange aperture is located in the porous medium. More particularly, the distal end collar 156 limits high pressure water and small particles to reach the water-repellent membrane 142. Then, the water-repellent membrane 142 prevents accidental liquid and porous medium infiltration which could have entered in the internal space defined by the distal end collar 156 and the protection sleeve 144 in the gas exchange channel 136 and the gas exchange aperture, and thereby prevents partial or complete obstruction of the gas exchange aperture which could bias the porous medium property measurements. While preventing accidental liquid and porous medium infiltration, the water-repellent membrane 142 allows gas communication therethrough.

In the embodiment shown and described above, the assembly including the gas exchange tubing 132, the electric wire sleeve 176, and the protection sleeve 144 is flexible. In some implementations, at least one of the gas exchange tubing 132, the electric wire sleeve 176, and the protection sleeve 144 can be a rigid component and the resulting assembly can be rigid or substantially rigid.

In the implementation shown in FIGS. 1 to 5, the porous medium sensor 120 is a tensiometer and the gas exchange aperture is in fluid communication with a reference port of the pressure sensor mounted in the housing 124. It is appreciated that even if the above described embodiment relates to tensiometers, the assembly including the gas exchange tubing, the water-repellent membrane, the protective sleeve, and the end collar can be mounted to various types of sensing portions such as and without being limitable pH, salinity, temperature, humidity, liquid, gas, or gas concentration sensing portions wherein gas communication between two sections or between a section and atmosphere is wanted while, simultaneously, preventing liquid and porous medium infiltration. The sensing portion can also include a sensor detecting the irrigation status. The sensing portion can also include a LED photo detector for detecting fluid in soils or porous media.

The assembly including the gas exchange tubing, the water-repellent membrane, the protective sleeve, and the end collar can be used with modular or single piece sensor apparatuses and with self-priming or filled fluid chamber sensor apparatuses, and any combination thereof. It is appreciated that the water-repellent membrane can be replaced by any liquid repellent membrane which is designed to prevent liquid and porous medium infiltration in the gas exchange channel.

Moreover, although the embodiments of the porous medium sensor and corresponding parts thereof consist of certain geometrical configurations as explained and illustrated herein, not all of these components and geometries are essential to the invention and thus should not be taken in their restrictive sense. It is to be understood, as also apparent to a person skilled in the art, that other suitable components and cooperation therein between, as well as other suitable geometrical configurations, may be used for the porous medium sensor according to the present invention, as will be briefly explained herein and as can be easily inferred therefrom by a person skilled in the art. Moreover, it will be appreciated that positional descriptions such as "above", "below", "left", "right" and the like should, unless otherwise indicated, be taken in the context of the figures and should not be considered limiting.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention. The scope of the invention is therefore intended to be limited solely by the scope of the appended claims.

The invention claimed is as follows:

1. A porous medium sensor comprising:
a sensing portion at least partially insertable in a porous medium and having a housing with a gas exchange aperture defined therein and a parameter sensor mounted in the housing for measuring a parameter of the porous medium in which the sensing portion is insertable;
a gas exchange tubing in gas communication with the gas exchange aperture of the sensor portion and having a water-repellent membrane inserted therein, the water-repellent membrane preventing water infiltration in the housing through the gas exchange aperture;
a gas permeable protection sleeve covering at least a section of the gas exchange tubing; and
a water impermeable distal end collar covering a distal end of the gas permeable protective sleeve and the water-repellent membrane.

2. The porous medium sensor as claimed in claim 1, wherein the gas permeable protection sleeve covers the gas exchange tubing proximate to the water-repellent membrane.

3. The porous medium sensor as claimed in claim 1, wherein a gas chamber is defined between the water-repellent membrane and the water impermeable distal end collar, the gas chamber being in gas communication with the gas permeable protection sleeve.

4. The porous medium sensor as claimed in claim 3, wherein a gas channel is defined between the gas permeable protection sleeve and the gas exchange tubing and the gas channel being in gas communication with the gas chamber and the water-repellent membrane.

5. The porous medium sensor as claimed in claim 1, wherein the water-repellent membrane is inserted in an open-ended gas exchange channel extending through the gas exchange tubing, wherein a first open and proximal end of the gas exchange channel is aligned with the gas exchange aperture and a proximal end of the gas exchange tubing is sealed to the housing, and wherein the water-repellent membrane is inserted in the gas exchange channel close to a distal end of the gas exchange tubing.

6. The porous medium sensor as claimed in claim 1, wherein the gas permeable protection sleeve comprises a peripheral wall including a metal wire mesh component.

7. The porous medium sensor as claimed in claim 1, further comprising a proximal end collar covering a proximal end of the gas permeable protection sleeve and at least a section of the gas exchange tubing.

8. The porous medium sensor as claimed in claim 1, wherein the water impermeable distal end collar is a polymeric heat-shrinkable collar.

9. The porous medium sensor as claimed in claim 1, further comprising at least one electric wire extending outwardly from the housing and having at least a section thereof covered by the gas permeable protection sleeve.

10. The porous medium sensor as claimed in claim 9, wherein the at least one electric wire extends through and past the water impermeable distal end collar.

11. The porous medium sensor as claimed in claim 1, wherein the water-repellent membrane is porous and gas permeable and the gas exchange tubing comprises a polymeric water and gas impermeable peripheral wall.

12. The porous medium sensor as claimed in claim 1, wherein the parameter sensor is selected from the group comprising: an electrical transducer, a pressure sensor, a H+-selective transducer, an ion-selective transducer, a temperature sensor, a humidity sensor, a liquid sensor, and a gas sensor.

13. The porous medium sensor as claimed in claim 1, wherein the gas exchange tubing is flexible and orientable to extend above the housing and allowing gas exchange between atmosphere and the gas exchange aperture.

14. A porous medium sensor comprising:
- a sensing portion at least partially insertable in a porous medium and having a housing with a gas exchange aperture defined therein and a parameter sensor mounted in the housing for measuring a parameter of the porous medium in which the sensing portion is insertable;
- a gas exchange tubing having a gas and water impermeable wall defining a gas exchange channel in gas communication with the gas exchange aperture of the sensing portion and a water-repellent membrane inserted in the gas exchange channel, the water-repellent membrane preventing water infiltration in the gas exchange channel through a distal open end of the gas exchange tubing;
- a gas permeable sleeve covering at least partially the gas exchange tubing and allowing gas communication with the water-repellent membrane; and
- a water impermeable distal end collar covering at least a section of the gas permeable sleeve and a section of the gas exchange tubing including the water-repellent membrane to prevent water infiltration therein.

15. The porous medium sensor as claimed in claim 14, wherein the water-repellent membrane is inserted in the gas exchange channel close to the distal open end of the gas exchange tubing and the gas permeable sleeve covers the water-repellent membrane.

16. The porous medium sensor as claimed in claim 14, wherein a gas chamber is defined between the water-repellent membrane and the water impermeable distal end collar, the gas chamber being in gas communication with the gas permeable sleeve and wherein a gas channel is defined between the gas permeable sleeve and the gas exchange tubing and the gas channel being in gas communication with the water-repellent membrane through the gas chamber.

17. The porous medium sensor as claimed in claim 14, wherein a proximal open end of the gas exchange channel is aligned with the gas exchange aperture and a proximal end of the gas exchange tubing is sealed to the housing.

18. The porous medium sensor as claimed in claim 14, wherein the gas permeable sleeve comprises a peripheral wall including a metal wire mesh component.

19. The porous medium sensor as claimed in claim 14, further comprising at least one electric wire extending outwardly from the housing and having at least a section thereof covered by the gas permeable sleeve and wherein the at least one electric wire extends past the water impermeable distal end collar.

20. The porous medium sensor as claimed in claim 14, wherein the parameter sensor is selected from the group comprising: an electrical transducer, a pressure sensor, a H+-selective transducer, an ion-selective transducer, a temperature sensor, a humidity sensor, a liquid sensor, and a gas sensor.

* * * * *